(12) United States Patent
Niemeyer

(10) Patent No.: US 7,133,605 B2
(45) Date of Patent: Nov. 7, 2006

(54) HEATER FOR SCENTED CANDLES

(75) Inventor: Andrew Niemeyer, Churchville, MD (US)

(73) Assignee: Crazy Mountain Imports, Inc., Imlay City, MI (US)

( * ) Notice: Subject to any disclaimer, the term of this patent is extended or adjusted under 35 U.S.C. 154(b) by 0 days.

(21) Appl. No.: 11/028,786

(22) Filed: Jan. 4, 2005

(65) Prior Publication Data

US 2005/0150886 A1    Jul. 14, 2005

Related U.S. Application Data

(60) Provisional application No. 60/535,867, filed on Jan. 12, 2004.

(51) Int. Cl.
*A61M 16/00* (2006.01)
*F27D 11/00* (2006.01)

(52) U.S. Cl. .................................. 392/390; 219/438

(58) Field of Classification Search ............... 392/386, 392/390, 391, 392, 393; 219/477, 480, 482, 219/490, 438, 429, 441, 442, 402, 406, 409
See application file for complete search history.

(56) References Cited

U.S. PATENT DOCUMENTS

| | | | | |
|---|---|---|---|---|
| 3,636,310 A | * | 1/1972 | Hosokawa et al. | ......... 219/501 |
| 3,876,861 A | * | 4/1975 | Wightman et al. | ........ 219/458.1 |
| 4,571,485 A | * | 2/1986 | Spector | ...................... 392/390 |
| 4,937,431 A | * | 6/1990 | Jameson et al. | ............. 392/395 |
| 5,175,791 A | * | 12/1992 | Muderlak et al. | ............ 392/390 |
| 6,100,504 A | * | 8/2000 | Wagner | ...................... 219/432 |
| 6,354,710 B1 | | 3/2002 | Nacouzi | ....................... 362/96 |
| 6,627,857 B1 | | 9/2003 | Tanner et al. | ............. 219/445.1 |
| 2003/0209533 A1 | | 11/2003 | Tanner et al. | ................ 219/445 |

OTHER PUBLICATIONS

"Candlewarmers.com, 2005 Product Guide".

* cited by examiner

*Primary Examiner*—Sang Paik
(74) *Attorney, Agent, or Firm*—Honigman, Miller, Schwartz and Cohn LLP

(57) ABSTRACT

Disclosed herein is a device for heating a scented candle so as to release scent therefrom in the absence of an open flame. The device includes a housing for retaining the candle. The housing is fabricated from a material having a low thermal conductivity. The device further includes an electrical heater in thermal communication with the housing. The heater warms the candle, and the low thermal conductivity housing aids in retaining heat in the candle thereby causing scent to be released therefrom.

26 Claims, 2 Drawing Sheets

HEATER FOR SCENTED CANDLES

REFERENCE TO RELATED APPLICATION

This patent application claims priority of U.S. provisional patent application Ser. No. 60/535,867, filed Jan. 12, 2004, and entitled "Candle Warmer."

FIELD OF THE INVENTION

This invention relates generally to heating devices. More specifically, the invention relates to a heating device which is operable to receive and retain a scented candle and to maintain it at an elevated temperature relative to an ambient temperature so as to facilitate the dispersal of scent therefrom.

BACKGROUND OF THE INVENTION

Scented candles release an aroma into the ambient atmosphere when burned, and are increasing in popularity. Such candles are often used for enhancing the ambience or mood in the home or workplace. Despite their popularity, there are some perceived problems associated with the burning of scented candles. The presence of an open flame can present hazards to children and pets, and burning candles present a fire hazard and should not be left unattended. Also, the smoke produced by burning candles can present a health or a nuisance hazard, and can complicate respiratory problems for particular individuals. Furthermore, smoke from the burning candle can damage or discolor furniture, walls and fabrics. Thus, it will be seen that while the effects of scented candles are desirable, there are problems associated with the open flame attendant upon their use.

Consequently, the prior art has sought to implement solutions whereby a candle's scent may be released without the requirement of utilizing an open flame. Toward that end, the prior art has investigated various designs of candle warming devices which allow scented candles to flamelessly disperse their aroma. The previous implementation of such a candle heater comprised the use of miniature hotplates, of the type employed for heating individual beverage cups; and in such instance, the candle, which is typically contained in a glass vessel, is placed onto the hotplate. In some instances, these hotplate-type candle warmers have a collar which surrounds a portion of the length of the candle; but they are not designed to enclose the entire length of the candle. This approach is less than satisfactory since only the bottom portion of the candle is heated. As a consequence, it takes a relatively long time to melt the upper surface of the candle wax so as to release the scent. This lag time can be shortened if the heat level of the hotplate is raised to a fairly high value; however, these high heat levels can pose a burn hazard once the candle is fully warm. Also, high heat levels can start to vaporize the candle wax thereby generating unwanted odors and damaging fumes. In addition, the heated wax fumes can present a significant fire hazard. Hotplate-type candle warmers are shown, for example, in U.S. Pat. No. 6,627,857. Another prior art approach to warming scented candles involves the use of a radiant heater which projects infrared light onto an upper surface of the candle. Devices of this type are relatively complicated and energy inefficient. Radiant candle heaters are shown in U.S. Pat. No. 6,354,710.

As will be explained hereinbelow, the present invention is directed to a flameless candle heating device which efficiently and safely retains scented candles and the like and warms them to a uniform temperature optimized for safety and release of scent. These and other advantages of the invention will be apparent from the drawings, discussion and description which follow.

BRIEF DESCRIPTION OF THE INVENTION

There is disclosed herein a device for retaining and heating a scented candle or other body of scented hydrocarbon material. The device includes a housing which is fabricated from a body of a low thermal conductivity material. The housing has a substantially open top and comprises at least one sidewall and a base, which cooperate to define a partially enclosed interior volume which is configured to receive and retain the entire length of a candle therein. The device further includes an electrical heater which is in thermal conductivity with the housing. The heater is operable to warm the body of scented hydrocarbon material so that its scent exits through the open top of the housing.

The housing may, in some instances, be a unitary body, while in other instances it may comprise an assembly of multiple pieces. The housing has a relatively low thermal conductivity, as defined herein, and may, in some instances, be fabricated from a body of ceramic material. In other instances, it may comprise a relatively high thermal conductivity material such as a metal combined with a body of insulating material.

In specific embodiments, the device can include a temperature controller for regulating its operation, as well as other features, such a pilot light, an on/off switch, and the like.

DETAILED DESCRIPTION OF THE INVENTION

The present invention comprises a device for uniformly heating a scented candle so as to release its aroma, without the necessity of employing an open flame. The device of the present invention includes a housing which is fabricated from a body of low thermal conductivity material, as will be explained and defined hereinbelow. The low thermal conductivity housing encloses a scented candle. The device further includes an electrical heater which is in thermal communication with the housing. The housing operates to retain heat and allows the heater to uniformly heat the entire body of the candle without generating large temperature extremes. Since the housing shields the heated candle, it provides additional safety.

Figure 1:
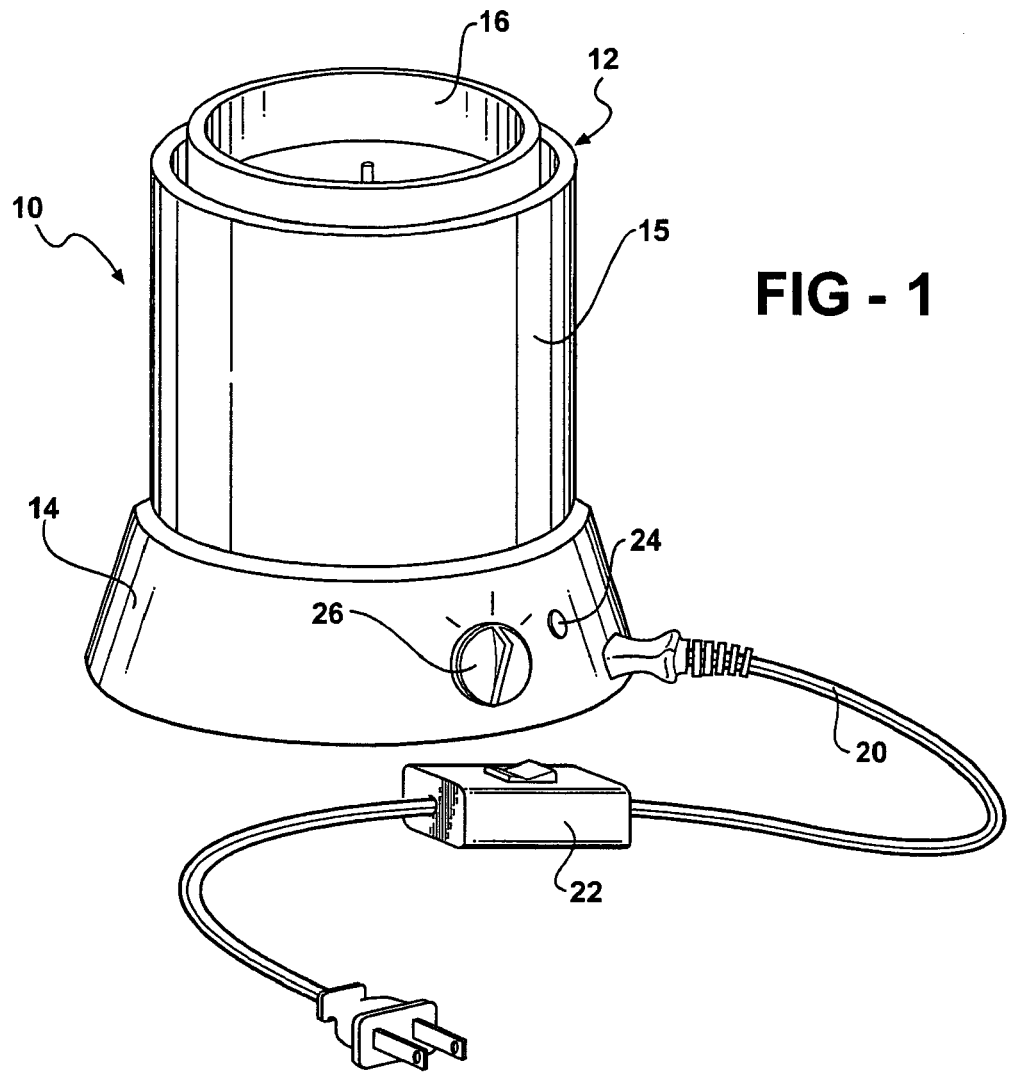
FIG. 1 is a perspective view of one embodiment of a candle warming device structured in accord with the principles of the present invention.

Referring now to FIG. 1, there is shown a perspective view of one embodiment 10 of a candle heater structured in accord with the principles of the present invention. As will be seen, the warming device 10 includes a body 12 which includes a base portion 14 which is integral therewith. The body 12 has a generally cylindrical sidewall 15 which cooperates with the base portion thereof 14 to define and enclose an interior volume. In specific embodiments, this interior volume is sufficiently large so as to contain substantially all of the length of a candle disposed therein. The configuration of the body 12 is such that its top is substantially open so as to permit the insertion of a candle 16 thereinto. The substantially open top also facilitates the dispersal of aroma from the candle 16 in the operation of the device. It is to be understood that the top is shown as completely open in these figures; however, the top may be partially covered by a perforated plate, a mesh, or other such covering, provided that the covering has significant open space therethrough to permit dispersal of the aroma. As such, the presence of top members of this type does not preclude the top from being defined as "substantially open."

The device of FIG. 1 includes a power cord 20 for connecting its heater (not shown in this drawing) to a source of electrical power. As illustrated, the power cord includes an on/off switch 22; although, this item is an option in the present invention. The warmer 10 of FIG. 1 also includes an indicator light 24 which is lit when the heater is energized so as to provide a visual indication of the operation of the device. This is also an optional feature of the present invention. Another optional feature of the present invention is a temperature control device such as the dial control 26 shown in FIG. 1. This control allows the user of the device to regulate the temperature of the heater. In other embodiments, this temperature controller may be eliminated. In yet other embodiments, temperature control may be automatic, by means of a thermostat, thermistor, or similar device.

Figure 2:
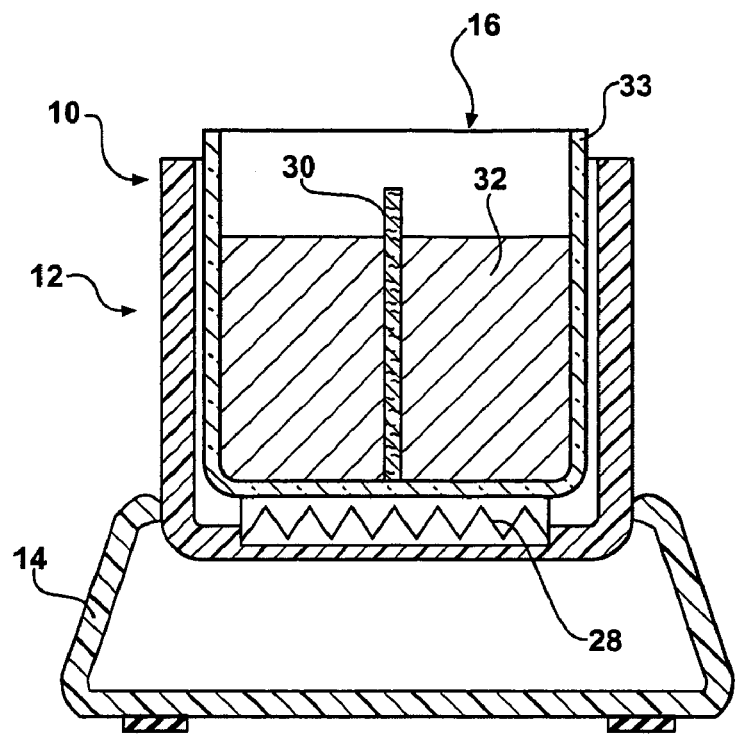
FIG. 2 is a cross-sectional view of the device of FIG. 1 taken along section line A—A.

Referring now to FIG. 2, there is shown a cross-sectional view of the warming device 10 of FIG. 1 taken along line A—A. As will be seen, the device 10 includes a body portion 12 which further includes a base 14 integral therewith. The body portion is fabricated, at least in part, from a material having a low thermal conductivity. In general, a low thermal conductivity is understood to be a thermal conductivity less than that of steel. Steel and other iron alloys typically have a thermal conductivity in the range of 0.16 $(cal/sec)/(cm^{2\circ} C./cm)$. Most typically, the low thermal conductivity materials of the present invention have a thermal conductivity which is less than 0.01 $(cal/sec)/(cm^{2\circ} C./cm)$, and in particular instances, have a thermal conductivity which is less than 0.005 $(cal/sec)/(cm^{2\circ} C./cm)$. Ceramics are one low thermal conductivity material which may be utilized in the present invention, and a typical thermal conductivity for such ceramic materials is in the approximate range of 0.005–0.001 $(cal/sec)/(cm^{2\circ} C./cm)$. Other low thermal conductivity materials include various polymers, which term also encompasses polymer-based composites, such as glass or mineral filled polymers, or polymer coated materials such as metals, provided that such structures fall within the definition of low thermal conductivity.

Shown in the FIG. 2 embodiment is an electrical heater 28 which is disposed at the bottom of the interior volume enclosed by the housing 12. Although not shown in this view, it is understood that this heater is in electrical communication with a source of electrical power via a power cord or the like, as is better shown in FIG. 1.

As can be seen from FIG. 2, a scented candle 16 is disposed within the body 12 so as to be heated by the heater 28. As shown, the candle 16 includes a wick 30 and a body of scented wax 32. Since the heater of the present invention eliminates the need for burning the candle, the wick 30 may be eliminated. It is also to be understood that the body of wax 32 may be replaced by an oil or other such hydrocarbon material which will dissolve and retain a scent agent.

Accordingly, it is to be understood that within the context of this disclosure, the term "scented candle" is to be interpreted very broadly so as to include all bodies of scented hydrocarbon material, both liquid and solid, whether they include a wick or not.

Figure 3:
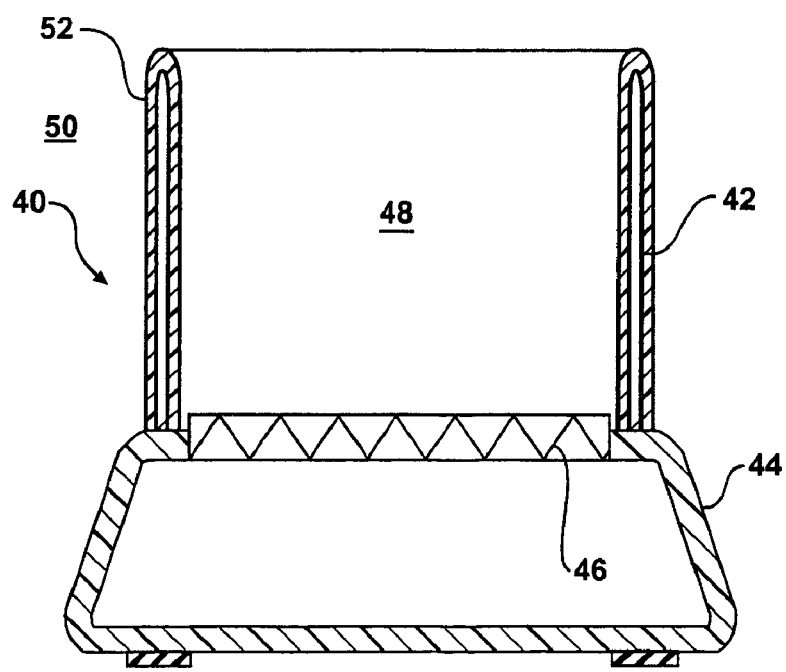
FIG. 3 is a cross-sectional view of another embodiment of a heating device of the present invention.

The present invention may be implemented in various embodiments, and FIG. 3 illustrates one other embodiment of candle warmer 40 structured in accord with the present invention. The FIG. 3 embodiment includes a two-part housing comprised of a sidewall member 42 disposed upon a base 44 which has an electrical heater 46 supported thereupon. As in the previous embodiment, the housing defines an interior volume 48 which is substantially open at its top and which is configured to receive and retain a candle (not shown) therein.

The FIG. 3 embodiment also differs from the FIGS. 1 and 2 embodiment insofar as the sidewall portion of the housing 42 is fabricated from a relatively high thermal conductivity material such as sheet metal; but, it is further configured to define an insulating air space 50 between opposed wall portions 52. This enclosed space 50 may be left empty, or may be filled with an insulating material such as a glass or a mineral fiber. The thermal conductivity of the material (air or insulating fiber) in the enclosed space 50 is very low. Hence, the overall thermal conductivity of the sidewall member 42 is low, within the definitions established herein. Yet other variations of the present invention may be likewise implemented.

Figure 4:
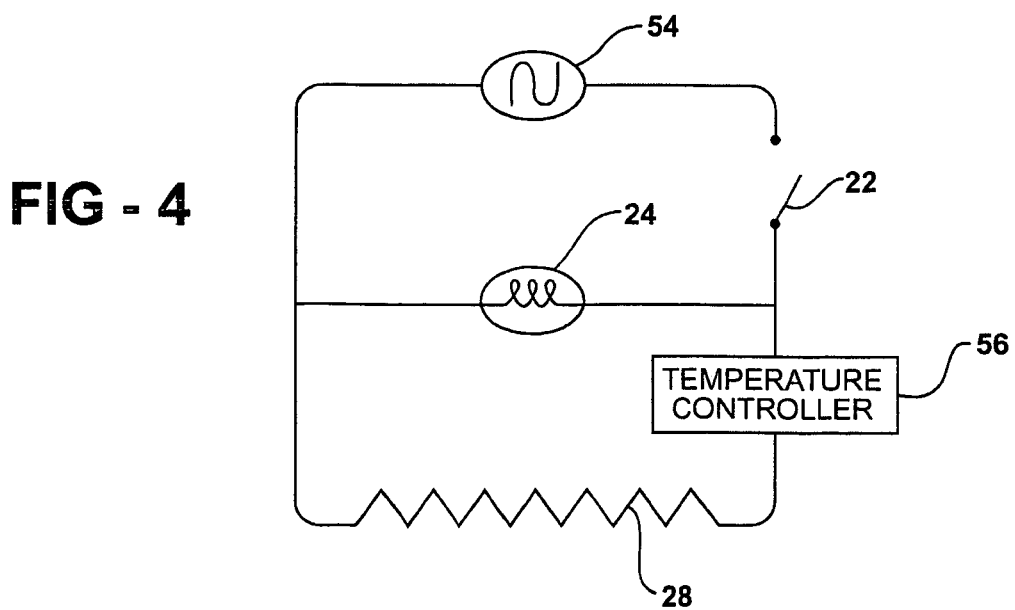
FIG. 4 is a schematic depiction of one circuit which may be used to energize the electrical heater in warming devices of the present invention.

Referring now to FIG. 4, there is shown a schematic diagram of one circuit which may be employed for energizing the electrical heater used in the device of the present invention. Shown in FIG. 4 is an electrical heater 28 which is electrically energized, in this case, by a source of alternating current 54. An electrical switch 22 allows for the selectable energization of the heater 28. A pilot light 24 is also electrically connected to the generator 54 via the switch 22 so that the light will be lit whenever the heater 28 is energized.

Also shown in FIG. 4 is a temperature controller 56 which is associated with the heater 28. The temperature controller 56 operates to regulate the flow of electrical energy to the heater 28, thereby controlling the temperature of the heater. In some instances, the temperature controller may comprise a thermostat having a preset temperature point, and will operate to maintain the heater at a preselected temperature. In one embodiment, the temperature of the heater is regulated so that the body of hydrocarbon material in the device of the present invention does not exceed 75° C. In other instances, the temperature controller may comprise a thermostat which can be user-set to a desired temperature. In yet other instances, the temperature controller may comprise a variable resistor which a user can set to control the temperature of the heater. In yet other instances, the temperature controller may comprise a temperature responsive electronic device such as a thermistor.

In one mode of operation of the present invention, the temperature controller 56 may operate to initially energize the heater at a fairly high power level to provide for a rapid initial temperature rise in the heating device; and, the controller will further operate so that when a target temperature is reached, the power to the heater will be stepped-down to a lower level sufficient to maintain a desired temperature. Yet other modifications and variations of the power circuit will be readily apparent to those of skill in the art.

It is to be understood that the foregoing drawings, discussion and description are illustrative of specific embodiments of the present invention, but are not meant to be limitations upon the practice thereof. In view of the teaching presented herein, numerous modifications and variations of the invention will be apparent to those of skill in the art. It is the following claims, including all equivalents, which define the scope of the invention.

The invention claimed is:

1. A system for retaining and heating a scented candle comprising:
   a scented candle having a bottom surface;
   a housing fabricated from a body of a low thermal conductivity material, said body having a substantially open top, and comprising at least one sidewall and a base, which cooperate to define an interior volume which is configured to receive and retain at least a portion of said scented candle therein, wherein said base has a vertical height, and said sidewall has a vertical height extending upwardly from said base that is at least equal to the vertical height of said base; and
   an electrical heater which is in thermal communication with said housing and at least a portion of said heater is disposed within a portion of said base, said heater being operable to provide direct conduction of heat to at least a portion of said bottom surface of said scented candle retained in said housing, so that scent therefrom exits the housing through the substantially open top.

2. The device of claim 1, wherein said housing comprises a unitary body.

3. The device of claim 1, wherein said housing comprises an assembly of at least two parts.

4. The device of claim 1, wherein said housing is comprised of a ceramic material.

5. The device of claim 1, wherein said housing includes a body of an insulating material associated therewith.

6. The device of claim 1, further including a switch for selectively energizing said electrical heater from a source of electrical power.

7. The device of claim 1, further including an indicator light which is in electrical communication with said electrical heater, said indicator light being operable to provide a visually detectable signal indicative of the energization of said heater.

8. The device of claim 1, further including a temperature controller which is in electrical communication with said heater, said temperature controller being operable to regulate the temperature of said heater.

9. The device of claim 8, wherein said temperature controller comprises a thermostat.

10. The device of claim 8, wherein said temperature controller comprises a variable resistor.

11. The device of claim 8, wherein said temperature controller comprises a thermistor.

12. The device of claim 1, wherein said housing defines an interior volume configured to receive and retain a scented candle which is disposed within a container separate from said housing.

13. The device of claim 1, wherein said housing is fabricated from a material having a thermal conductivity less than the thermal conductivity of iron.

14. The device of claim 1, wherein the housing is fabricated from a material having a thermal conductivity of less than 0.01 cal/sec/cm$^2$C/cm.

15. The device of claim 1, wherein said housing is fabricated from a material having a thermal conductivity of less than 0.005 cal/sec/cm$^2$C/cm.

16. The device of claim 1, wherein said housing has a generally cylindrical shape.

17. The device of claim 1, further including a temperature regulating circuit operative to regulate the operation of said heater so that the temperature of a body portion of said scented candle does not exceed 75° C.

18. The device of claim 1, wherein said heater is in direct contact with at least a portion of the bottom surface of said scented candle.

19. A system for retaining and heating a scented candle, said system comprising:
   a scented candle including a bottom portion;
   a candle-holding receptacle that supports said scented candle, said candle-holding receptacle including a bottom surface;
   a housing including a body comprised of a low thermal conductivity material, said body including a substantially open top, and comprising at least one sidewall and a base that cooperate to define an interior volume that is configured to receive said candle-holding receptacle such that a portion of said bottom surface of said candle-holding receptacle directly contacts a portion of said base; said base having a vertical height, and said sidewall having a vertical height extending upwardly from said base that is at least equal to the vertical height of said base; and
   an electrical heater that is in thermal communication with said housing, at least a portion of said heater is supported on or is disposed within a portion of said base; said heater being operable to provide conduction of heat from the heater to said bottom surface of said candle-holding receptacle such that heat is directly conducted from said candle-holding receptacle to said bottom portion of said scented candle and a scent produced from the heating of said scented candle exits the housing through the substantially open top.

20. The system of claim 19, wherein said housing comprises a unitary body.

21. The system of claim 19, wherein said housing is comprised of a ceramic material.

22. The system of claim 19, wherein said housing includes an insulating material.

23. The system of claim 19, wherein said heater is in direct contact with at least a portion of said bottom surface of said candle-holding receptacle.

24. The system of claim 19, including a switch for selectively energizing said electrical heater from a source of electrical power.

25. The system of claim 19, including an indicator light which is in electrical communication with said electrical heater, said indicator light being operable to provide a visually detectable signal indicative of the energization of said heater.

26. The system of claim 19, further including a temperature controller which is in electrical communication with said heater, said temperature controller being operable to regulate the temperature of said heater.

* * * * *

(12) EX PARTE REEXAMINATION CERTIFICATE (6756th)
United States Patent
Niemeyer

(10) Number: US 7,133,605 C1
(45) Certificate Issued: Apr. 7, 2009

(54) HEATER FOR SCENTED CANDLES

(75) Inventor: Andrew Niemeyer, Churchville, MD (US)

(73) Assignee: Crazy Mountain Imports, Inc., Imlay City, MI (US)

Reexamination Request:
No. 90/008,978, Dec. 31, 2007

Reexamination Certificate for:
Patent No.: 7,133,605
Issued: Nov. 7, 2006
Appl. No.: 11/028,786
Filed: Jan. 4, 2005

Related U.S. Application Data

(60) Provisional application No. 60/535,867, filed on Jan. 12, 2004.

(51) Int. Cl.
*A61M 16/00* (2006.01)
*F27D 11/00* (2006.01)

(52) U.S. Cl. .......................... 392/390; 219/438
(58) Field of Classification Search .......... None
See application file for complete search history.

(56) References Cited

U.S. PATENT DOCUMENTS

| | | | |
|---|---|---|---|
| 3,876,861 A * | 4/1975 | Wightman et al. | 219/458.1 |
| 4,937,431 A * | 6/1990 | Jameson et al. | 392/395 |
| 5,651,942 A | 7/1997 | Christensen | |
| 5,744,106 A | 4/1998 | Eagle | |
| 6,354,710 B1 | 3/2002 | Nacouzi | |
| 6,413,476 B1 | 7/2002 | Barnhart | |
| 6,627,857 B1 | 9/2003 | Tanner | |
| 7,132,084 B1 | 11/2006 | Roumpos | |

* cited by examiner

*Primary Examiner*—Joseph A. Kaufman

(57) ABSTRACT

Disclosed herein is a device for heating a scented candle so as to release scent therefrom in the absence of an open flame. The device includes a housing for retaining the candle. The housing is fabricated from a material having a low thermal conductivity. The device further includes an electrical heater in thermal communication with the housing. The heater warms the candle, and the low thermal conductivity housing aids in retaining heat in the candle thereby causing scent to be released therefrom.

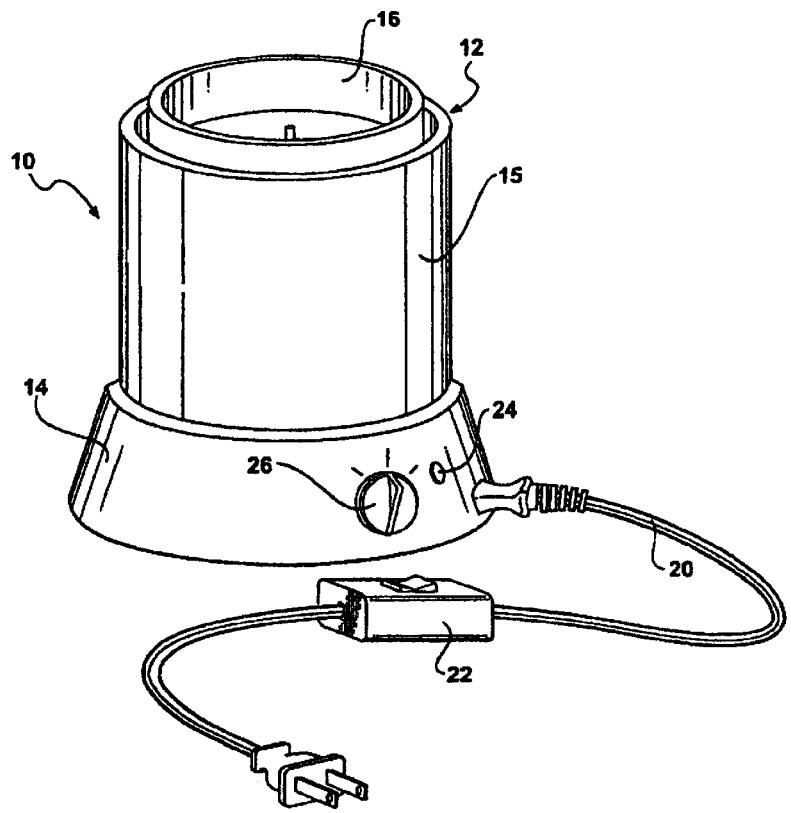

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–26 are cancelled.

* * * * *